United States Patent [19]

Martin et al.

[11] 4,337,039
[45] Jun. 29, 1982

[54] PLASTERLESS ARTICULATOR

[76] Inventors: Raymond H. Martin, 88 Brisbon Rd., Somerset, Mass. 02726; Ugo S. Garganese, 1790 Warwick Ave., Warwick, R.I. 02889; John R. Griffin, 5 Franconia St., Dorchester, Mass. 02122

[21] Appl. No.: 71,948

[22] Filed: Sep. 4, 1979

[51] Int. Cl.³ .............................................. A61C 11/00
[52] U.S. Cl. .......................................... 433/60; 433/34
[58] Field of Search ...................... 433/60, 57, 58, 61, 433/62, 63, 64, 65, 66, 67, 34

[56] References Cited

U.S. PATENT DOCUMENTS

| D. 204,381 | 4/1966 | Orofino | 433/63 |
|---|---|---|---|
| 2,423,522 | 7/1947 | Shumukler et al. | 433/58 |
| 2,535,146 | 12/1950 | Lyons | 433/66 |
| 2,786,272 | 3/1957 | Lindley | 433/60 |
| 3,221,408 | 12/1965 | Scullin | 433/60 |
| 3,653,126 | 4/1972 | Hansen | 433/60 |
| 3,722,099 | 3/1973 | Jankelson | 433/60 |
| 3,844,040 | 10/1974 | Willis | 433/60 |
| 3,975,489 | 8/1976 | Mercer | 264/16 |
| 4,169,314 | 10/1979 | Mercer et al. | 433/60 |

FOREIGN PATENT DOCUMENTS 1291854  4/1968  Fed. Rep. of Germany ........ 433/56

OTHER PUBLICATIONS

"Moyco"ad, N.A.D.L. Journal, 12-1968
"Artic-u-logic," Hagman, Dental Laboratory Review, pp. 18-22, 2-1981.
"History of Detal Laboratories," Rothstein, pp. 56-59.

Primary Examiner—Gene Mancene
Assistant Examiner—John J. Wilson

[57] ABSTRACT

A dental articulator for mounting stone models without the need of plaster, by the use of a flexible model former with a rim around its edge and a square raised nipple, a ferromagnetic disc, magnets and a square keying device on the articulator. This method permits rapid articulation. The models may also be removed and replaced at will while maintaining the previously established centric.

1 Claim, 8 Drawing Figures

PLASTERLESS ARTICULATOR

BACKGROUND OF THE INVENTION

This invention is directed to a new and novel plasterless articulator used in dentistry and specifically for use in the forming of dental restorations by a technician for the purpose of eliminating the work of plaster mixing and for attaching dental or other models in a fixed keyed position on the articulator.

It is also an object of this invention to allow the technician to remove and rearticulate the model by a special key technique allowed by this plasterless articulator that at present does not exist.

While plasterless articulators do exist, none, once removed has the ability to return to the same fixed position for accuracy since no successful key positioning exists.

The invention comprises a special articulator with the following capabilities: to be able to eliminate plaster work and plaster or other composition; to be able to accomplish the elimination of work and material and to key a model to a prefixed position such that after removal the model can be returned to the same prefixed position; furthermore, the model may be removed and returned in such a manner repeatedly without error.

This invention further comprises a model base former for preforming the base of the model to accept special attachments which will key lock the model to a prefixed position on the special articulator designed for this purpose, to allow removal for working on or transporting the model and to allow it to be returned to the same preset position.

This invention is an improvement over the present plasterless articulators since those that presently exist are of the kind that use vertical bolts and horizontal bolts to secure models to their articulators. Once removed, the models have to be reseated into a bite plane or matrix to be rearticulated. The present invention allows the model to be reseated into its keyed position with precision by use of a square holed model with a key lock retainer imbedded therein which is seated and held by magnet attraction. The operator can remove the models from the articulator giving freedom to work on the models separate from the articulation and return them to check articulation as often as desired with pecision without the need of a bite plane or matrix.

DESCRIPTION OF THE PREFERRED EMBODIMENTS

Figure 1:
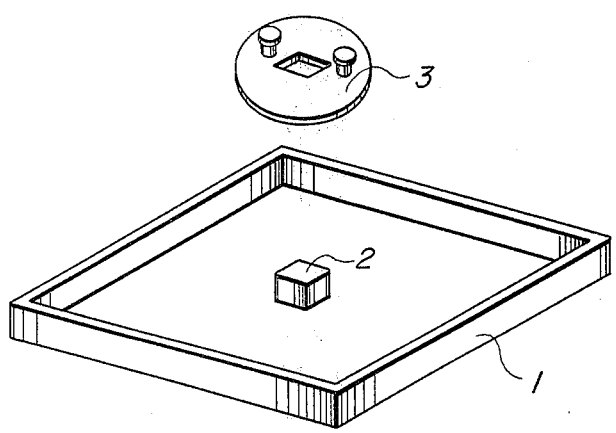
FIG. 1 shows a flexible model base former and ferromagnetic disc.
Figure 2:
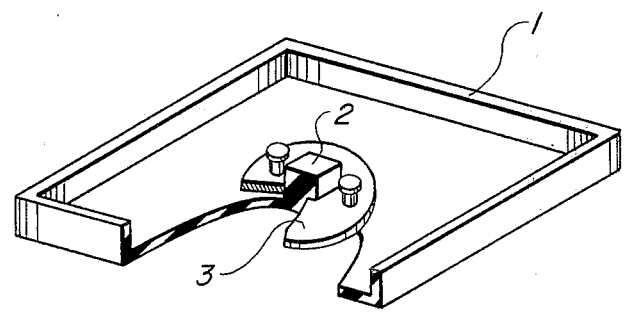
FIG. 2 illustrates combining ferromagnetic disc and the flexible model base former.
Figure 3:
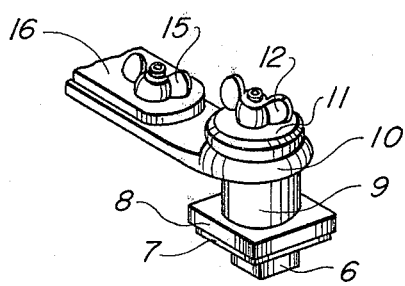
FIG. 3 shows keying effect of models to protruberances of upper and lower members of the plasterless articulator.
Figure 4:
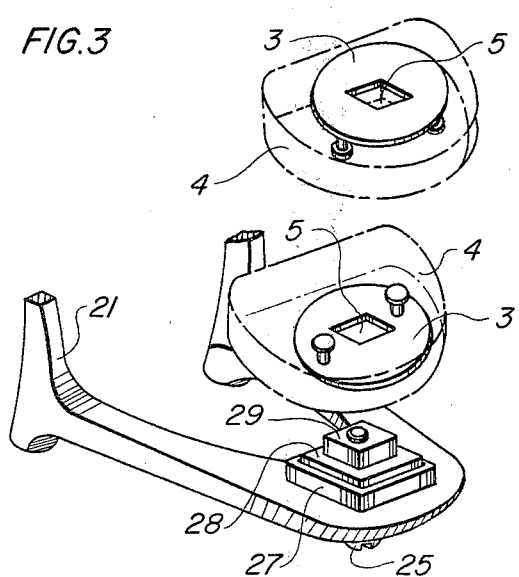
FIG. 4 shows a side view of the plasterless articulator.
Figure 4:
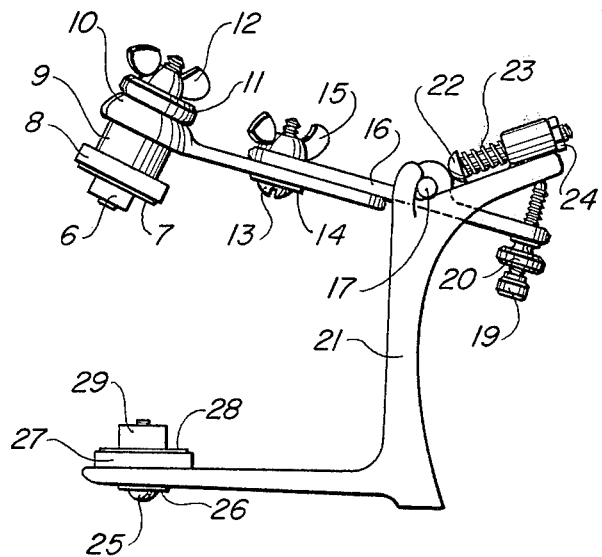
Figure 5:
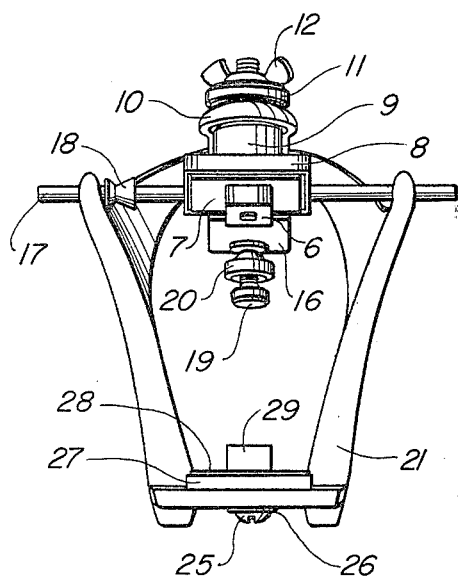
FIG. 5 shows a front view of the articulator with protruberances of the keying components and with the magnetic cap and the vertical setting bolt on the rear of the articulator.
Figure 6:
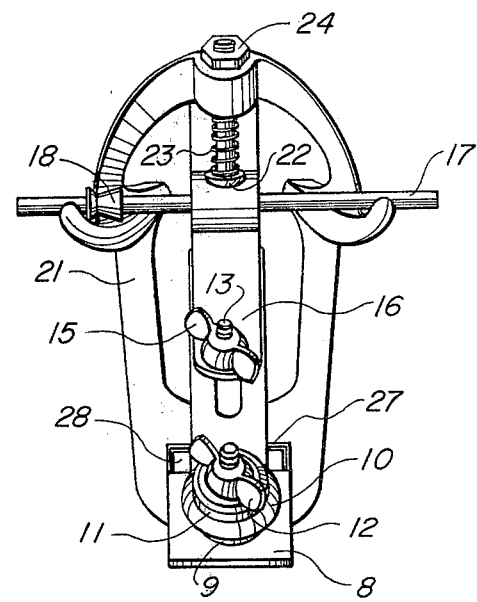
FIG. 6 shows the upper assembly of moveable components for quick adjustments.
Figure 7:
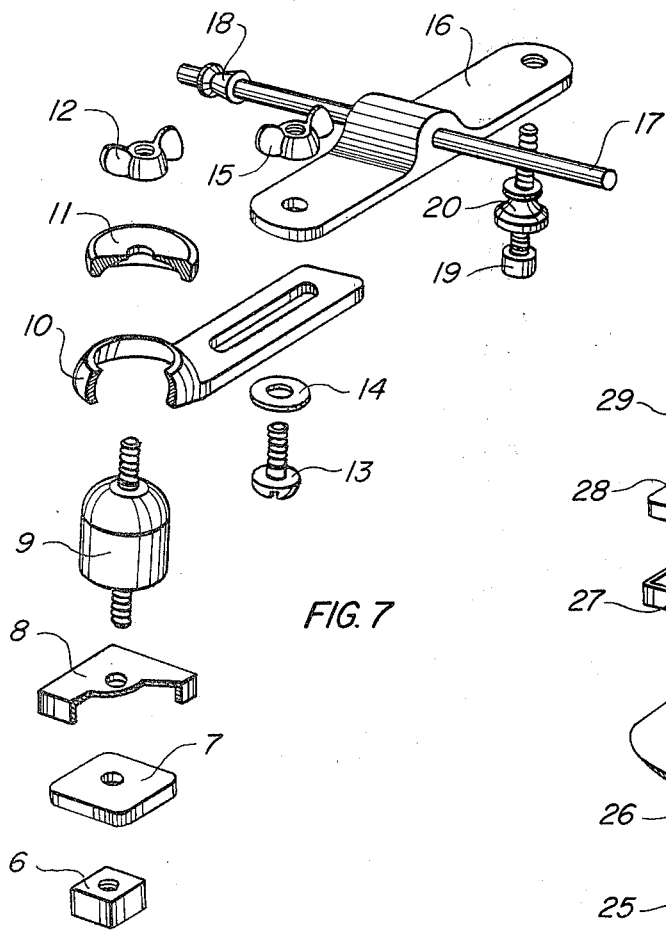
FIG. 7 shows component parts in sequence assembly of the upper section of the articulator.
Figure 8:
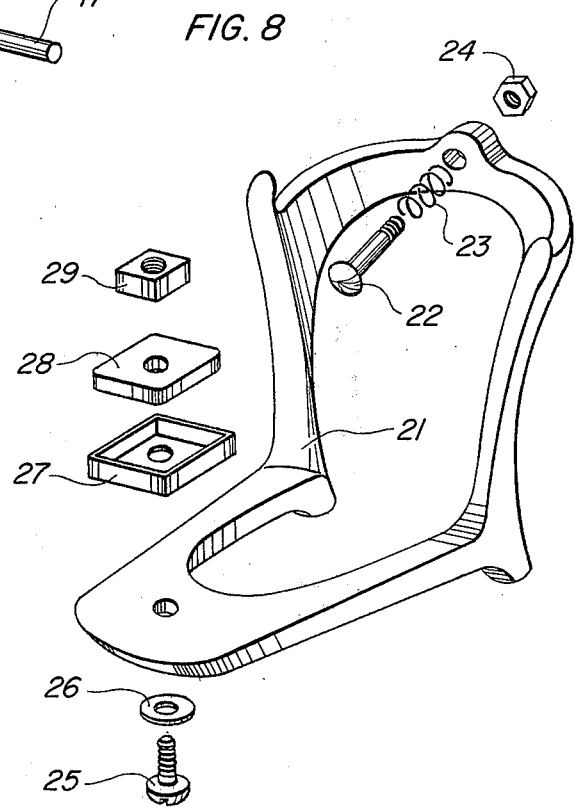
FIG. 8 shows component parts in sequence assembly of the lower section of the articulator.

FIG. 1 shows a model base former 1 to be placed beneath an impression which is poured of gypsum to create the model and a model key former 2 which forms a square hole in the base of the gypsum model. A metal key lock retainer 3 has a square hole the same size as the model key former 2 and includes retention grips as shown in FIG. 1 which imbed into the gypsum model when it is poured. FIG. 2 shows the model base former with the metal key lock retainer 3 placed in position over the model key former and ready for the gypsum to be poured. FIG. 3 shows the key lock retainer 3 imbedded in the gypsum model 4. The square hole 5 formed in the model by key former 2 will engage the square nut 6 (for the case of the upper model) and be held in the articulator by magnet 7 which has a metal magnet cover 8. A metal swivel dome 9 and swivel dome socket and housing slide bar 10 allow protrusive, retrusive, and radius movements for setting the articulator and includes a swivel socket housing washer 11 and wing nut 12 for locking the assembly into the desired position corresponding to the patient's bite registration. The slide bar 10 is locked into position on the slide bar supporting arm 16 by wing nut 15, see FIG. 4. The lower jaw frame 21 will similarly attach the lower jaw model, hole 5 engaging square nut 29 while being held by magnet 28 having cover 27 which are attached to the lower jaw frame 21 by a washer 26 and bolt 25. FIG. 4 shows the articulator, as can be seen the slide bar 10 is fixed to the slide bar supporting arm 16 by wing nut 15 washer 14 and bolt 13. The support arm 16 pivots on an axel pin 17, the pivoting being limited by rear pin vertical control bolt 19 and lock nut 20. The lower jaw frame 21 has a stabilizer pressing pin 22 and pressure spring 23 for holding and stabilizing arm 16. FIG. 5 shows a front view of the plasterless articulator while FIG. 6 shows a top view and FIGS. 7 and 8 show exploded views of the component parts for a clearer understanding thereof.

After the usual procedure of taking impressions of the upper and lower jaws and a wax bite of the relationship of the lower to the upper jaw, the operator places the metal key lock retainer 3 over the model key former 2 and proceeds to pour the gypsum material into the impressions and into the model base former 1 which is then allowed to harden. When the gypsum has hardened, it is separated from the assembly, which leaves the operator with the finished models 4 which contain the metal key lock retainer 3 and a formed square hole 5 in its base. By placing models on the bite registration of the patient's jaws, this assembly is mounted on the articulator in the following manner.

The underside of the lower model is engaged over the lower jaw square nut 29 and is seated on the magnet and magnet cover 28 and 27 which secures it to the articulator. The upper model is now engaged by loosening the slide bar wing nut 15 and metal swivel dome wing nut 12. The upper square jaw nut 6 is placed into the gypsum model square hole 5, thus engaging the upper magnet and magnet cover 7 and 8. The upper metal swivel dome 9 is then locked into this position by tightening wing nut 12 reaffirming the bite registration. The slide bar 10 will automatically position itself. The slide bar is then locked into this position by tightening the slide bar wing nut 15, completing the arrangement.

The bite registrations are now removed from the articulator, and the models are ready for setting teeth. The operator may remove the models at will to work on them apart from the articulator, giving the operator freedom of movement by not having to hold the articulator in his hands, the operator can, at will return the models to the articulator for checking his work.

We claim:

1. A plasterless dental articulator, model base former, ferromagnetic disc, for mounting and supporting an upper and lower dental models, said articulator comprising:

(A) A lower jaw frame, having a solid base to which a ferromagnetic cap with an encased square metal nut and magnet is attached to hold the lower model securely in place and, an upper jaw assembly consisting of a slide bar support having a horizontal axel with a lateral wheel on one end which attaches to the lower jaw frame to simulate the movement of the jaw; the slide bar support also having a threaded milled hole on either end, the distal hole to receive a vertical bolt and lock nut to establish the vertical opening of the upper and lower jaws; the anterior hole to receive a vertical bolt, a wing nut and a slide bar, said slide bar having an oblong opening inside most of its length which allows the slide bar to be moved fore, aft and laterally, the slide bar also having a cap shaped aperture with an opening on the anterior end through which an assembly of a swivel socket dome and machined domed washer is placed, with the upper portion of the assembly threaded to receive a wing nut to tighten the assembly and the lower portion having a ferromagnetic cap with an encased nut and a magnet to hold the upper model securely in place after which a slide bar and the swivel dome socket are tightened by means of the wing nuts, (B) A flexible model base former having a square nipple in the center the same demensions as the nut on the articulator and a wall along its edge the same height as the center nipple, (C) a ferromagnetic disc with retainers for securing into the base of the model and a square hole in the center, the exact dimensions to fit over the flexible nipple, so that the ferromagnetic disc will be transferred into the base of the model.

* * * * *